US00PP32700P2

(12) United States Plant Patent
Kordes

(10) Patent No.: US PP32,700 P2
(45) Date of Patent: Dec. 29, 2020

(54) MINIATURE ROSE PLANT NAMED 'KORPOT094'

(50) Latin Name: *Rosa hybrida*
Varietal Denomination: KORpot094

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/602,937

(22) Filed: Dec. 31, 2019

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749; A01H 5/02
See application file for complete search history.

(56) References Cited

U.S. PATENT DOCUMENTS

PP15,716 P2 4/2005 Kordes
PP29,042 P3 3/2018 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, herein referred to by its cultivar name, 'KORpot094', is provided which forms abundantly on a substantially continuous basis attractive, light pink colored blossoms. Attractive vigorous vegetative is formed, which contrasts beautifully with the blossoms. The growth habit is upright. The new variety is well suited for providing attractive ornamentation in the landscape.

1 Drawing Sheet

Botanical/commercial classification:
Latin name: *Rosa hybrida.*
Varietal denomination: 'KORpot094'.

The new variety of *Rosa hybrida* Miniature Rose Plant of the present invention was discovered in a cultivated area as a branch mutation of the variety 'KORpot064' (U.S. Plant Pat. No. 29,042) in March, 2019 at Surry, British Columbia, Canada.

It was found that the new variety of rose plant of the present invention possesses the following combination of characteristics:

(a) displays attractive, light pink colored blossoms,
(b) exhibits an upright growth habit, and
(c) forms vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORpot064' variety (i.e., the parent) displays darker pink colored blossoms and less petals compared to the new variety. Moreover, the new variety can be readily distinguished from other similar non-parental varieties. For example, the 'KORcarill' variety (U.S. Plant Pat. No. 15,716) displays darker pink colored flowers and a lower petal count compared to the new variety.

The new variety has been found to undergo asexual propagation in Surrey, British Columbia, Canada by a number of routes, such as vegetative cuttings. Asexual propagation techniques in Canada, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot094'.

The first offer for sale of the new variety was in the Spring of 2019.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately six weeks of age and was observed at Surrey, British Columbia, Canada while growing indoors on its own roots in a 4 inch container.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a six week old specimen of the new variety, observed during April, while growing in a 4 inch container on its own roots in a greenhouse in Cochranville, Pa.

Commercial classification: Miniature Rose Plant.

Plant:

*Habit*.—Upright.

*Height*.—Approximately 15.0 cm on average.

*Width*.—Approximately 12.0 cm on average.

Branches:

*Stem color*.—Commonly near Yellow-Green Group 144A.

*Length*.—Main stems: approximately 15.0 cm on average. — secondary stems: approximately 9.0 cm on average.

*Texture*.—Glabrous.

*Thorns*.—Young thorns: moderate amount; color is commonly near Orange Group 26C; length is approximately 5.0 mm on average; and width is approximately 2.0 mm on average at point of attachment.

Foliage:

*Young foliage color*.—Upper surface: commonly near Green Group 143A with indistinguishable venation. — under surface: commonly a blend of near Yellow-Green Group 146B and Greyed-Orange Group 176C with venation near Yellow-Green Group 146C.

*Old foliage color*.—Upper surface: commonly near Green Group 139A with indistinguishable venation. — under surface: commonly near Green Group 139B with venation near Green Group 139C.

*Petiole*.—Upper surface: texture is smooth; color is commonly near Green Group 137A. — under surface: texture is mostly smooth with sparse prickles; color is commonly near Green Group 137B.

*Rachis*.—Color: upper surface is commonly near Green Group 137A, under surface is commonly near Green Group 137B.

*Stipules*.—Length: approximately 7.0 mm on average. — width: approximately 4.0 mm on average. — margin: entire to erose. — color: upper surface is commonly near Green Group 137A, under surface is commonly near Green Group 137B.

*5-leaflet leaf*.—Length: approximately 8.0 cm on average. — width: approximately 6.0 cm on average.

*Leaf margin*.—Serrate.

*Glossiness of upper side of leaf*.—Semi-glossy.

Leaflets:

*Number of leaflets*.—3, 5, and 7.

*Shape*.—Ovate; apex is acute; and base is rounded.

*Arrangement*.—Odd-pinnate.

*Venation pattern*.—Reticulate.

*Texture*.—Upper and under surfaces is smooth.

*Terminal leaflet*.—Length: approximately 4.0 cm on average. — width: approximately 2.0 cm on average.

*Lower leaflet*.—Length: approximately 2.3 cm on average. — width: approximately 1.5 cm on average.

Inflorescence:

*Number of flowers*.—Generally about 7 blooms open on average on a plant at once.

*Number of blooms per stem*.—Typically 1-3 blooms per stem on average.

*Peduncle*.—Length: approximately 3.5 cm on average. — diameter: approximately 3.0 mm on average. — surface texture: glabrous. — strength: strong. — color: commonly near Yellow-Green Group 144A.

*Sepals*.—Number: commonly 5. — length: approximately 2.5 cm on average. — width: approximately 1.0 cm on average. — margin: entire with occasional extensions on two or three sepals measuring approximately 7.0 mm in length on average and 2.0 mm in width on average. — upper surface color and texture: commonly near Yellow-Green Group 144A; covered in short pubescence. — under surface color and texture: commonly near Yellow-Green Group 144A; puberulent. — shape: lanceolate. — apex: acute to aristate. — base: truncate or flat as it joins the receptacle.

*Bud*.—Shape: globular. — length: approximately 2.0 cm on average. — width: approximately 2.0 cm on average. — color when opening: commonly near Red-Purple Group 65B.

*Flower*.—Diameter: approximately 4.5 cm on average. — height: approximately 2.5 cm on average. — duration: flower is on the plant approximately 20-24 days. — form: double, cuplike. — profile: flat. — number of petals under normal conditions: approximately 136 petals on average. — shape of the petal: overall: broadly obovate. apex rounded to cuspidate. base: rounded to cuneate. — petal length: inner petals are approximately 1.0 cm on average; outer petals are approximately 2.5 cm on average. — petal width: inner petals are approximately 8.0 mm on average; outer petals are approximately 2.0 cm on average. — petal margin: entire. — petal drop: average. — fragrance: very light sweet fragrance. — petal color when first and fully open: upper surface: commonly near Red-Purple Group 65B with basal spot of near White Group 155B. under surface: commonly near Red-Purple Group 65C with basal spot of near White Group 155B. — petal color when fading: upper and under surfaces: commonly near White Group N155C. — petal texture: upper and lower surfaces are glabrous. — petaloids: typically 10 per flower; color of upper and under surfaces is commonly near Red-Purple Group 65B with basal spot of near Yellow Group 4D; length is approximately 5.0 mm on average; width is approximately 3.0 mm on average; texture is smooth; margin is variable, entire to erose; shape is rounded and mostly curving inward; apex is round; base is cuneate.

*Receptacle*.—Color commonly near Yellow-Green Group 144A. — diameter: approximately 8.0 mm on average. — surface texture: smooth. — shape: urn shaped.

*Stamen*.—Number is approximately 50 on average. — anthers: number is approximately 50 on average; color is commonly near Yellow-Orange Group 15C; length is approximately 1.5 mm on average; and shape is oval. — filaments: length is approximately 1.5 mm on average and color is commonly near Yellow Group 10B.

*Pistils*.—Arrangement is separate and free; number is approximately 120 on average. — styles: length is approximately 5.0 mm on average; color is commonly near Yellow Group 5B at the base and transitioning to near Red Group 45D at the apex. — stigmas: diameter is typically less than 1.0 mm; color is commonly near Yellow Group 13B; shape is fan shaped.

*Pollen*.—None observed.

*Hips*.—None observed.

Development:

*Vegetation*.—Dark green, vigorous and strong.

*Blooming*.—Abundant and continuous.

*Hardiness*.—Unknown.

*Resistance to disease*.—Good resistance to *Botrytis* (*Botrytis cinera*) disease under normal greenhouse growing conditions in Cochranville, Pa.

Plants of the 'KORpot094' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) displays attractive, light pink colored blossoms, (b) exhibits an upright growth habit, and (c) forms vigorous vegetation;

substantially as herein shown and described.

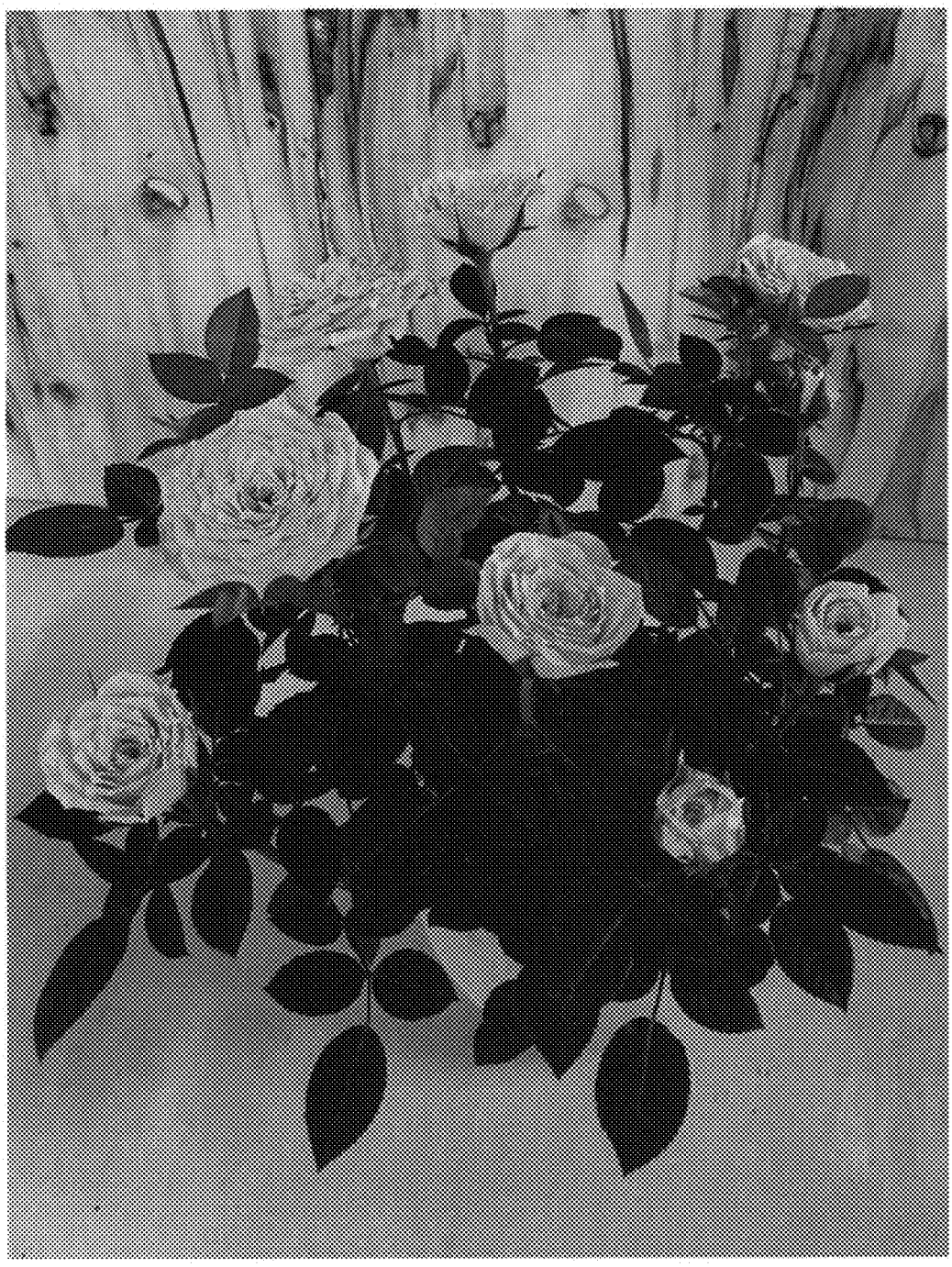

* * * * *